(12) United States Patent
Katz

(10) Patent No.: US 8,063,026 B2
(45) Date of Patent: Nov. 22, 2011

(54) METHOD OF PALLIATING LOWER URINARY TRACT INFECTIONS BY TREATMENT WITH MANNAN OLIGOSACCHARIDES

(76) Inventor: Richard Katz, Richmond, CA (US)

( * ) Notice: Subject to any disclaimer, the term of this patent is extended or adjusted under 35 U.S.C. 154(b) by 1229 days.

(21) Appl. No.: 11/544,244

(22) Filed: Oct. 6, 2006

(65) Prior Publication Data

US 2007/0244069 A1 Oct. 18, 2007

Related U.S. Application Data

(60) Provisional application No. 60/790,028, filed on Apr. 6, 2006.

(51) Int. Cl.
*A01N 43/04* (2006.01)
*A01N 65/00* (2006.01)
*A61K 31/727* (2006.01)
*G01N 33/53* (2006.01)

(52) U.S. Cl. ............ 514/54; 514/23; 514/56; 514/61; 514/618; 424/771; 435/7.31

(58) Field of Classification Search .................. None
See application file for complete search history.

(56) References Cited

U.S. PATENT DOCUMENTS

| 5,939,279 | A | * | 8/1999 | Smith et al. ............... 435/7.32 |
| 6,143,300 | A | | 11/2000 | Stevenot |
| 6,753,319 | B2 | * | 6/2004 | Benedict et al. ............. 514/35 |
| 7,048,937 | B2 | | 5/2006 | Dawson et al. |

OTHER PUBLICATIONS

Davis, M.E., et al., "Dietary supplementation with phosphorylated mannans improves growth response and modulates immune function of weanling pigs", 2004, Journal of Animal Science, 82, pp. 1882-1891.*
Parkkinen, J., eta;., "Identification of factors in human urine that inhibit the binding of E. Coli adhesions", 1988, Infection and Immunity, 56:10, pp. 2623-2630.*
Aronson, M., et al., Prevention of colonization of the urinary tract of mice with E. Coli by blocking of bacterial adherence with methyl alpha-D-mannopyranoside, 1979, 139:3, pp. 329-332.*
Wright, J.V., et al., "D-Mannose and Bladder Infection", 2001, d-mannoseworks.com, pp. 1-16.*
Abraham, D.J, et al., "Swainsonine affects the processing of glycoproteins in vivo", 1983, FEBS, 163(1), pp. 110-113.*
Halasz, A., et al., "Use of Yeast Biomass in Food Production", 1991, CRC Press, p. 31.*
Health Marketplace Website, Accessed by internet archive, "http://web.archive.org/web/20040805135721/http://www.health-marketplace.com/Probiotic-Blend.htm" Aug. 5, 2004, pp. 1-2.*
Head, K.A., et al., "Natural Approaches to Prevention and Treatment of Infections of the Lower Urinary Tract", 2008, Alternative Medicine Review, 13, pp. 227-244.*
Foxman, B., et al. 2000. Ann. Epidemiol. 10:509-15.
Manges, et al. 2001. NEJM, 345:1007-1013.
Sotelo, TM and Westney, OL, 2004. "Recurrent Urinary Tract Infections in women"; Women's Healthcare, pp. 2-6.
Stamm and Wooten, 1993. NEJM 329:1328.
Gupta, et al. 1999. JAMA 281:736-738.
Shibata,N., et al. 1996. JBC 271-9259.
Okawa, Y, et al. 2006. Biol. Pharm. Bull. 29:388.
Shibata, N., et al. 1996. Arch.Biochem Biophys. 336:49.
Rozeboom, et al. 2005. J. Anim. Sci. 83:2637.
Holland, 1990. Clin Microb. Rev. 3:345.
Stewart, et al. Rec. Dev. in Pig Nutrition, "Recent Advances in Probiosis in Pigs: Observ. on the Microbio.of the Pig Gut", pp. 51-77, Nottingham Univ. press, Nottinham,UK.
Spring, et al., 2000. Poult. Sci. "The Effects of Dietary Mannanoligosaccharides on Cecal Parametes . . . " 79:205.
Savage and Zakrzewska, 1996. Poul. Sci. "The Performance of Male Turkeys Fed a Starter . . . " pp. 47-54.
Peppler, H.J., 1979. Microbial Technology & Microbial Processes, vol. 1 (2nd Ed.) "Production of Yeasts and Yeast Products." p. 157.
Feiz, L., et al. 2006. Plant Methods "Evaluation of cell wall preparations for purifying ell walls from *Arabidopsis* hypocotyls" 2:10.
Davis, et al. 2004. J. Anim. Sci. "Dietary Supplementation with phosphorylated mannans improves . . . " 82:1882.
Whistler, RI and J Saarnio Galactomannan from soy Bean Hulls 1957 J. Am. Chem. Soc. 79:6055-6057.
McCleary, BV Enzymatic Hydrolysis, Fine Structure, and Gelling Interaction of Legum-Seed D-Galacto-D-Mannans 1979 Carbo. Res. 71:205-230.
Stephen Barrett, MD, The American Quack Association (http://www.quackwatch.com/04ConsumerEducation/Nonrecorg/aqa.html).
Weiner, MH and WJ Yount, Mannnan Antigenemia in the Diagnosis of Invasive Candida Infections, 1976 J. Clin. Invest. 58:1045-53.
Kilpatrick, DC, Mannan-Binding Lectin: Clinical Significance and Applications 2002 Biochim. et Biophys. Acta 1572:401-413.
Beutler, E. and L. Teeple, Mannose Metabolism in the Human Erythrocyte, J. Clin. Invest. 1969 48:461-466.

* cited by examiner

Primary Examiner — Michael G Hartley
Assistant Examiner — Lance Rider
(74) Attorney, Agent, or Firm — David Dolberg

(57) ABSTRACT

Provided herein are methods of using mannan oligosaccharides, to treat, palliate, relieve, prevent and/or eliminate urinary tract infections of humans. A mixture of oligosaccharides derived from yeast cell walls is shown to reduce, eliminate and prevent the symptoms of UTI in patients.

8 Claims, 2 Drawing Sheets

A - Oligomannose 5 Control

B - Oligomannose 5 Digest

A - BioMOS® Control

B - BioMOS® Digest

C - Digest Control

METHOD OF PALLIATING LOWER URINARY TRACT INFECTIONS BY TREATMENT WITH MANNAN OLIGOSACCHARIDES

CROSS REFERENCE TO RELATED APPLICATIONS AND CLAIM OF PRIORITY

This is a U.S. utility application filed under 35 U.S.C. §111(a) and claiming the benefit of U.S. Provisional Application No. 60/790,028, filed 6 Apr. 2006, under 35 U.S.C. §111(b), as a basis for priority under 35 U.S.C. §119(e).

FIELD OF THE INVENTION

This invention pertains to the treatment of urinary tract infections. Particularly, it pertains to methods of palliating, relieving and eliminating the symptoms of lower urinary tract infections in human patients. More particularly, it pertains to the oral administration of yeast-derived mannan oligosaccharides (MOS).

BACKGROUND OF THE INVENTION URINARY TRACT INFECTION

Infections of the Urinary Tract (UTI) are extremely common. UTIs are the second most common reason for physician visits, and account for about 8.3 million doctor visits each year. (Ambulatory Care Visits to Physician Offices, Hospital Outpatient Departments, and Emergency Departments: United States, 1999/2000. Vital and Health Statistics. Series 13, No. 157. Hyattsville, Md.: National Center for Health Statistics, Centers for Disease Control and Prevention, U.S. Dept. of Health and Human Services; September 2004.) Men, women and children develop UTIs. Evidence indicates that urinary tract infections are due to enterobacteria, principally *Escherichia coli*.

Symptoms of UTI include a frequent urge to urinate and a painful, burning feeling in the area of the bladder or urethra during urination. It is not unusual to feel bad all over—tired, shaky, washed out—and to feel pain even when not urinating. Often women feel an uncomfortable pressure above the pubic bone, and some men experience fullness in the rectum. It is common for a person with a urinary infection to complain that, despite the urge to urinate, only a small amount of urine is passed. The urine itself may look milky or cloudy, even reddish if blood is present. Normally, a UTI does not cause fever if it is in the bladder or urethra. A fever may mean that the infection has reached the kidneys. Other symptoms of a kidney infection include pain in the back or side below the ribs, nausea, or vomiting.

UTIs usually occur when bacteria enter the opening of the urethra and multiply in the urinary tract. The urinary tract includes the two kidneys, ureters (tubes that carry urine from the kidneys to the bladder), the bladder itself, and the urethra (the tube that carries urine from the bladder to the urethral opening). A UTI limited to the urethra is called urethritis. If the infection migrates to the bladder it is called cystitis. If the infection migrates to the kidneys it is called pyelonephritis. Infections of any and all urinary tract components as described are considered UTI herein and the methods of the present invention are effective treatments and preventions for each and all.

Women are more prone to UTIs than men, probably because they have shorter urethras, which therefore pass bacteria into the urinary tract more easily. Statistics show that one in every five women will develop a UTI during her lifetime. Although the estimated prevalence of UTI varies, all reports indicate a staggering number of female UTI sufferers: 7 to 11 million women, or 7 to 11 percent of adult women in the U.S., visit their physicians for a UTI each year. Overall 20 to 60 percent of women will have at least one UTI over their lifetime. After having one UTI, up to 20 to 30 percent will suffer from recurrent infections. Sexually-active women are especially prone to UTIs and recurrent UTIs (Foxman, B., et al. 2000. Ann. Epidemiol. 10:509-15; Foxman, B. 1990. Am. J. Pub. Health, 80:331-333; Manges et al. 2001. NEJM, 345: 1007-1013; Sotelo T M, and Westney O L, 2004. Women's Healthcare, 2004, 2-6). Women who have had more than three UTIs are likely to continue to develop recurrences within 18 months of a UTI. In severe cases this can be even more frequent.

Urinary tract infections most commonly occur in the bladder (cystitis, or "honeymoon disease"), and uncomplicated UTI is usually caused by strains of *Escherichia coli* (*E. coli*). In healthy women with uncomplicated cystitis, the usual treatment includes three days of antibiotics. The typical drugs chosen are: trimethoprim (Trimpex®), trimethoprim-sulfamethoxazole (Bactrim DS® by Roche, Septra, Cotrim), amoxicillin (Amoxil, Trimox, Wymox), nitrofurantoin (Macrobid® by Proctor and Gamble, Furadantin), ampicillin (Omnipen, Polycililin, Principen, Totacillin), ofloxacin (Floxin), norfloxacin ((Noroxin), ciprofloxacin (Cipro® by Bayer), trovafloxin (Trovan) and levofloxacin (Levaquin® by Ortho-McNeil). Recurrent UTIs can be treated with a low dose of antibiotics following intercourse, or by taking daily or thrice-weekly antibiotics for six months to several years (Stamm and Hooten, 1993. NEJM 329:1328). Clinical management of UTI is complicated by the increasing incidence of infections caused by *E. coli* that are resistant to commonly used antibiotics (especially trimethoprim-sulfamethoxazole). In recent studies, 15 to 22 percent of UTI cases were antibiotic resistant (Manges, supra; Gupta et al., 1999. JAMA 281:736-8). Furthermore, frequent use of antibiotics will also affect immune system functioning. A healthy immune system is important in the prevention of UTI. This means that antibiotics used to cure UTI may make another infection more likely in the near future. So-called "alternative remedies have also be suggested (See, e.g. Stevenot, U.S. Pat. No. 6,143,300)

There is some suggestion that one factor behind recurrent UTIs may be the ability of bacteria to attach to cells lining the urinary tract. A recent NIH-funded study found that bacteria formed a protective film on the inner lining of the bladder in mice. Another line of research has indicated that women who are "non-secretors" of certain blood group antigens may be more prone to recurrent UTIs because the cells lining the vagina and urethra may allow bacteria to attach more easily. (http://kidney.niddk.nih.gov/kudiseases/pubs/utiadult/)

Men are not as prone to UTIs as women, but infections are still common. The prostate gland in men produces secretions that retard the growth of bacteria. While men develop UTIs less frequently than women, their infections tend to be more severe. UTIs in men are often caused by an obstruction (e.g. a urinary stone) or an enlarged prostate. Prostate-related UTIs are more difficult to cure via conventional means because many antibiotics do not easily penetrate infected prostate tissue.

The outer cell walls of yeast are comprised entirely of mannose and N-acetyl glucosamine (as the disaccharide chitobiose), these sugars being linked to proteins to form a coat of glycopeptides. Mannose is the predominant sugar, hence the outermost layer of the cell wall of yeast may be said to consist of mannoproteins; and the carbohydrate part of these mannoproteins is generally called "mannan". A molecule of mannan may be comprised of hundreds if not thousands of mannose molecules, all linked together in chains and branches of chains. The covalent mannose-mannose bonds found in yeast mannan are primarily in the alpha configuration, the exception being the mannose to chitobiose beta linkage, where the N-linked mannan is anchored to protein of the cell wall at asparagine residues. (O-linked mannan has mannan anchored directly to protein at serine and threonine residues, no chitobiose at the anchor point, no beta linkages at all.) Covalent mannose-mannose bonds, found in side chains of *Candida* species, e.g. *C. guilliermondii* have been shown to be of the beta configuration and to be immunogenic (Shibata, N. et al. 1996. JBC 271:9259).

Yeast mannan, the above mentioned carbohydrate portion of yeast cell wall mannoprotein, is a polysaccharide. Upon fractionation to shorter chains, a polysaccharide yields oligosaccharides (shorter chains) and monosaccharides (simple sugars). An empirical mixture of oligosaccharides derived from yeast cell wall mannan is generally referred to as yeast mannan oligosaccharide, or MOS. MOS has been known to animal husbandry as a feed additive promoting weight gain in herds of various livestock, including pigs, cattle, rabbits, and chickens.

Mannan has been known to science as a determinant of immunogenicity. A yeast's mannan determines the immunogenicity for a given yeast, in no doubt the same fashion the high mannose glycosylation found on proteinaceous material generally provokes the immune response. The linkages and mannan structures of different yeast species and the same species grown under different conditions are different. (Shibata, N., supra; Okawa, Y. et al. 2006. Biol. Pharm. Bull. 29:388; Shibata, N. et al. 1996. Arch. Biochem Biophys. 336:49)

For the past several decades, carbohydrate biochemists have labored to elucidate the structure of mannans using mannan immunogenicity as a tool. However, with regard to the disease itself, mannan immunogenicity is a two edged sword: All or part of the structure of a mannan has been elucidated by assaying the immunogenicity of the oligosaccharides that comprise it, and carbohydrate biochemists have also explored the immune response itself. However, it is indeed the immune response to the high mannose glycosylation found on adventitious agents that render bioengineered polypeptides useless or dangerous to patients and cause the bioengineered products to be treated as foreign invaders akin to viruses, toxins, or mere filth.

MOS has been used in animal husbandry as a feed supplement. Several manufacturers produce MOS as an alternative to antibiotics for cattle and poultry feed, among them Bio MOS® (Alltech Biotechnology, Nicolasville, Ky.), CitriStim™ (Archer Daniels Midland Alliance Nutrition, Inc., Quincy, Ill.), and Agrimos® (Lallemand Animal Nutrition, Blagnac, France). A farmer adds this to the animal's feed, at the rate of a few pounds of additive per ton of feed, and the animal puts on weight just as though it were being dosed with the usual prophylactic low levels of antibiotics, maybe even a little better than antibiotic. Bio MOS® and Agrimos® are made from *Saccharomyces cerevisiae* yeast, common baker's yeast; CitriStim is made from *Candida guilliermondii* yeast; Species of both *Saccharomyces* and *Candida* are quite popular amongst molecular and cell biologists. Agrimos® is obtained by the autolysis of yeast cells at high temperatures and at a controlled pH. After autolysis is completed, cell wall and yeast extracts are separated by centrifugation, and cell wall is spray dried.

The theory behind use of MOS in husbandry is that farm animals suffer from a continual massive colitis. Bacteria— *Escherichia coli*, mostly—so infect the large intestine of livestock that getting rid of the infecting bacterial pathogens can actually give them a semblance of health. As described by Rozeboom et al. (J. Anim. Sci. 2005. 83:2637), many bacteria possess fimbriae, which are specific surface lectins that bind to the mucosal surface of the intestine to facilitate proliferation of the bacteria (Holland, 1990. Clin. Microb. Rev. 3:345); Stewart et al. 2001. Recent Dev. In Pig Nutrition 3, pgs 51-77, Nottingham Univ. Press, Nottingham, UK) Type I fimbriae specifically bind to glycoproteins that contain mannose. Bio MOS® has been shown to bind, in vitro, to bacterial cells possessing Type I fimbriae—particularly including *E. coli* (Newman, 1994. Proc. Alltech's $10^{th}$ Annul. Symp.: Biotechnology in the Feed Industry; Nottingham press, Nottingham, UK; Spring et al., 2000. Poult. Sci. 79:205). Bio MOS® has also been shown to alter immune function (Savage and Zakrzewska, 1996. Poult. Sci. 75:143; David et al., 2004).

Recently, compositions of MOS and methods of use have been disclosed for control of cocccidiosis in poultry (U.S. Ser. No. 07/048,937).

SUMMARY OF THE INVENTION

The instant invention claims methods of using the outer cell walls of yeast, and degradative and digestive products of the outer cell walls of yeast—also known as mannan oligosaccharides, and synthetic mannan oligosaccharides, to treat, palliate, relieve prevent and/or eliminate urinary tract infections of humans. A mixture of oligosaccharides derived from yeast cell walls is shown to reduce, eliminate and prevent the symptoms of UTI in patients.

It is an object of the present invention to provide simple methods for the treatment of urinary tract infections in humans, particularly in female patients.

It is an object of the present invention to provide simple methods for the treatment of urinary tract infections by oral administration of yeast-derived mannan oligosaccharides and mannan oligosaccharides.

It is an object of the present invention to provide simple methods for the relief of the symptoms of urinary tract infections in human patients by oral administration of mannan oligosaccharides.

It is an object of the present invention to provide simple methods for the relief of the symptoms of urinary tract infections in human patients by oral administration of the degradational preparations of the outer cell walls of yeast.

It is an object of the present invention to provide simple methods for the relief of the symptoms of urinary tract infections in human patients by oral administration of enzymatic digestional preparations of the outer cell walls of yeast.

It is an object of the present invention to provide simple methods for the prevention of urinary tract infections in humans, particularly in female patients.

It is an object of the present invention to provide simple methods for the prevention of urinary tract infections by oral administration of yeast-derived mannan oligosaccharides and mannan oligosaccharides.

It is an object of the present invention to provide simple methods for the prevention of symptoms of urinary tract infections in human patients by oral administration of mannan oligosaccharides.

It is an object of the present invention to provide simple methods for the prevention of symptoms of urinary tract infections in human patients by oral administration of the degradational preparations of the outer cell walls of yeast.

It is an object of the present invention to provide simple methods for the prevention of symptoms of urinary tract infections in human patients by oral administration of enzymatic digestional preparations of the outer cell walls of yeast.

Now therefore in consideration of the objects provided above, and other objects described herein, a method is provided for treating a patient to relieve symptoms of urinary tract infection comprising administration of an effective amount of mannan oligosaccharide.

Furthermore, a method is provided for preventing a patient from developing symptoms of urinary tract infections comprising administration of an effective amount of mannan oligosaccharide.

DETAILED DESCRIPTION OF THE INVENTION

Figure 1:
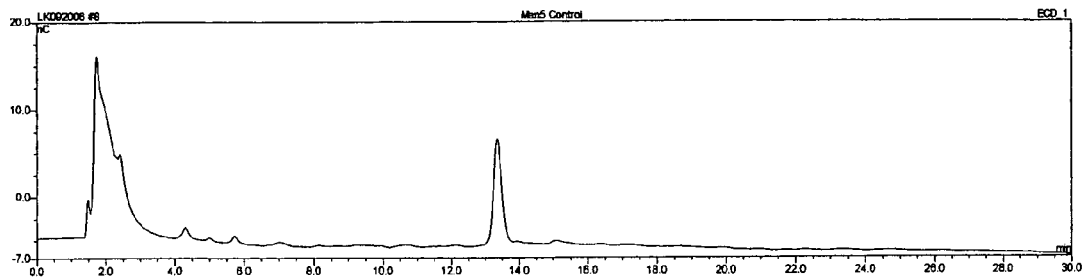
FIG. 1—HPLC Profiles of Digested and Undigested Oligomannose.
Figure 1:
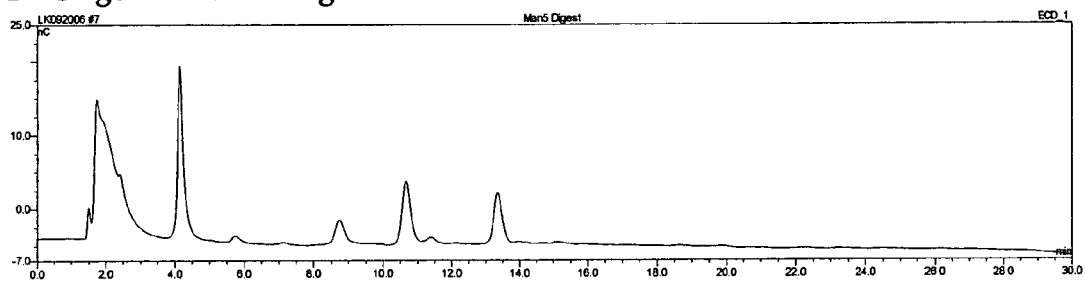

Any of a variety of yeast is appropriate for the preparation of MOS. Particularly useful is any of the species of *Saccharomyces*, most particularly, cerevisiae, or any of the species of *Candida*, most particularly *guilliermondii*. Yeast MOS is prepared in a variety of methods commonly known to those skilled in the art. Yeast cells are grown following common techniques used in food-related fermentations and in the beverage industry. Complex media allowing for rapid proliferation of the yeast cells are used. Any of a number of common sugar-containing media, such as diluted molasses, can be used for cell growth. Other medium components may be employed including corn, wood sugars, sulfite waste liquor, and whey. Once the population of yeast cells is expanded, the yeast cell wall extract, containing MOS, is prepared by methods commonly known in the art. (See, for example, Peppler, H. J. 1979. Production of Yeasts and Yeast Products. Page 157 in: *Microbial Technology & Microbial Processes*, Vol. 1 ($2^{nd}$ Ed.), Academic Press). Once concentrated from the growth medium, the yeast cells are lysed by any number of methods commonly used in the art. These include autolysis, hydrolysis or mechanical means such as freeze-thaw, extrusion, sonication and the like. After lysis, the cell wall material is collected by centrifugation. The cell wall extract may then be purified by a variety of methods known to those in the art. See for example, Feiz, et al. 2006. Plant Methods 2:10). The cell wall extract may be further degraded by mechanical or enzymatic methods known to those in the art. For partial or complete enzymatic degradation, the enzyme alpha-mannosidase, derived from jack beans is most useful. The specificity of this enzyme cleaves alpha-(1-2,3,6)-linked mannose, the common linkages of mannan oligosaccharides. By means of controlled enzyme degradation, MOSs of desired oligomer size can be prepared. Oligomers of no more than 10 subunits are desirable, preferably no more than 5-mers are desirable. The MOS component of the present invention may be obtained by a variety of methods—all contemplated within the scope of the present invention. MOS may be derived as a preparation of yeast outer cell, as a degradation or digestion of yeast outer cell wall preparation, as a purification of specific mannan oligosaccharides or as a synthetic product of mannose subunits.

MOS has been used in animal husbandry and is generally regarded as safe (GRAS). Cell wall extracts or purified cell wall extracts are then prepared in pharmaceutical compositions for administration to patients. Pharmaceutical compositions may be prepared as tablets, in gelatin capsules or as a powder. For tablets, MOS is mixed with a binder, generally starch-based, using methods commonly known in the art. The tablets may be prepared in a time-release or extended-release formulation. The tablets may additionally be prepared with a starch-based coating or other coating to make ingestion more palatable. Preparation of gelatin capsules is also commonly known to the art. These too may be prepared in a time-release or extended release formulation. The pharmaceutical composition may be preserved, cryopreserved, lyophilized, refrigerated, or the like. More specifically, MOS may also be provided in a dried or freeze-dried formulation. This formulation may be ingested with food or drink by the patient.

An effective amount of MOS is a dosage and frequency of ingestion sufficient to palliate, relieve or eliminate symptoms of urinary tract infection (UTI), or to prevent recurrence of UTI symptoms or to prevent a patient from developing symptoms of UTI. An effective dosage of MOS may be administered one to four times daily, preferably once or twice daily. An effective dosage of MOS is generally between about 0.1 milligram (mg) per kilogram (kg) of patient body weight and 100 mg per kg of patient body weight. Preferably, the dosage is between about 1 mg and about 20 mg. More preferably, the dosage is between about 2 mg and about 10 mg per kg of patient body weight.

Treatment of UTI with MOS will depend on the type and severity of symptoms. Typically, a patient will take an initial dosage of 2 mg to 20 mg of MOS per kg of body weight, preferably 4 mg/kg body weight, 2 to 4 times daily, until symptoms subside. Subsequently, a maintenance dosage of 1 mg to 10 mg of MOS per kg of body weight, preferably 2 mg/kg of body weight, one to three times daily, preferably two times daily at least until symptoms are eliminated or for at least about six months thereafter. Should symptoms return, the procedure is repeated.

MOS may be used prophylactically to prevent UTI symptoms. One mg to 10 mg of MOS per kg of body weight, preferably 2 mg/kg of body weight, is taken one to three times daily, preferably two times daily.

As used herein, "palliate" and "relieve" are used interchangeably to mean reducing the subjective experience of symptoms of an infection, syndrome or disease. As used herein, "eliminate" is used to mean the relief of symptoms of an infection, syndrome or disease to the point at which the patient no longer feels an effect of said infection, syndrome or disease. As used herein, "prevent" means prophylactic protection against the occurrence of symptoms of an infection, syndrome or disease.

EXAMPLES

The following examples further illustrate the invention. They are merely illustrative of the invention and disclose various beneficial properties of certain embodiments of the invention. These examples should not be construed as limiting the invention.

Example 1

Preparation of MOS

Yeast-derived compositions are prepared using cells of *S. cerevisiae* strain NCYC 1026 (American Type Culture Collection, Manassas, Va., Accession No. 46885; Agricultural Research Service, Peoria, Ill., NRRL Accession No. Y-11875). The yeast cell wall extract is obtained by methods commonly known in the art. Yeast are grown following common techniques known in the art in media allowing for rapid proliferation of the yeast cells. The yeast cells are then separated from the spent medium by centrifugation, for example, washed and again collected to yield a "yeast cream". Following separation, the cells in the yeast cream are lysed. The yeast cell suspension is diluted with water to a concentration of 10-12% dry solids and then heated to a temperature of 140° F. The pH is adjusted to approximately 8.5, with sodium hydroxide. A protease such as papain or any of a number of alkaline or neutral proteases can be added during the lysis phase to accelerate the solubilization of yeast proteins in the disrupted cell material. After an initial incubation with a protease, generally about 2 hours, the pH is adjusted to about 8.0 and the temperature of the mixture is slowly increased to approximately 158° F. The mixture is held at about 158° F. for about 30 min. The resulting yeast cell wall-containing particulate material is collected by centrifugation to remove low molecular weight intracellular components and concentrate the cell wall extract. The resulting concentrate is dried (by any of a number of methods common in the art, including spray-drying or drum drying) to form a hygroscopic, water-soluble powder.

Example 2

5 ug of BioMOS® was digested with 20 mU of alpha-mannosidase from jack bean (which removes alpha-(1-2,3, 6)-linked mannose) in 50 mM sodium phosphate, pH 5.0 overnight at 37 C. Two ug of the digest (or a mock digest without enzyme) was injected onto a Carbopac PA1 column equilibrated in 100 mM sodium hydroxide with 10 mM sodium acetate. Oligosaccharides were eluted using a linear gradient over 60 minutes from 10 mM to 125 mM sodium acetate in 100 mM sodium acetate at a flow rate of 1.0 mL/minute. Oligosaccharides were detected using pulsed-amperometric detection.

Figure 2:
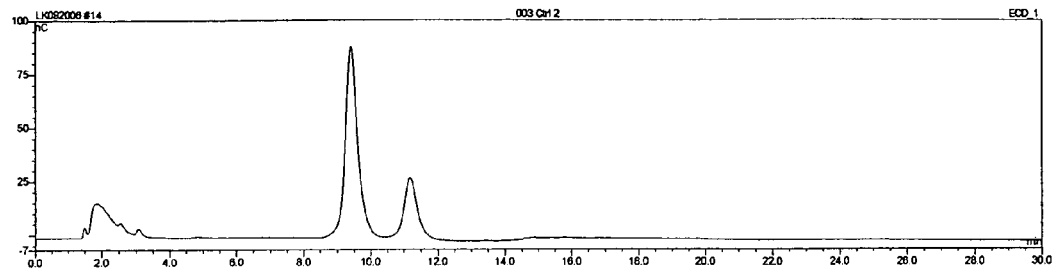
FIG. 2—HPLC Profiles of Digested and Undigested Bio-MOS®
Figure 2:
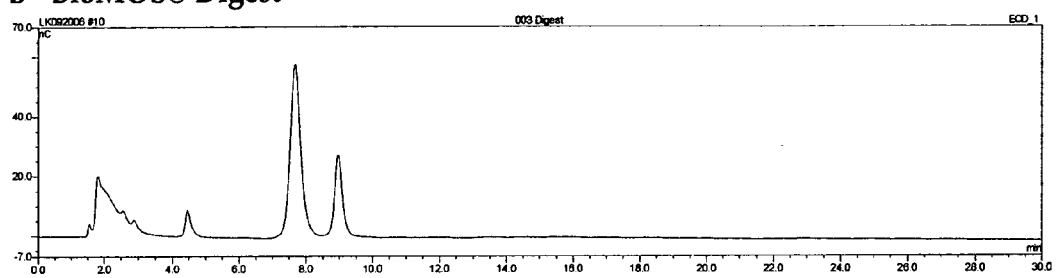
Figure 2:
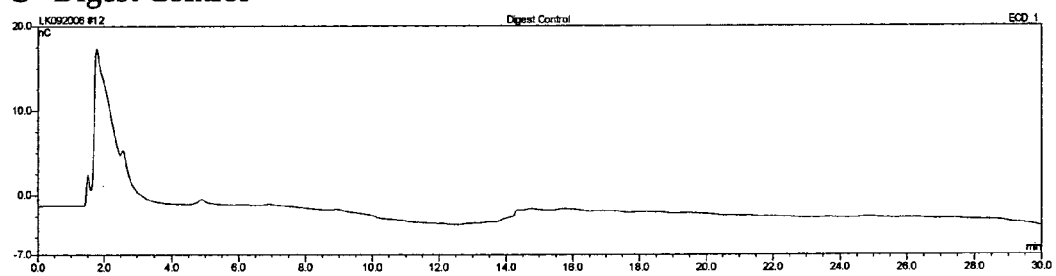

The way in which a 5-mer of oligomannose runs under these conditions on an HPLC column is shown in FIG. 1 and demonstrates the presence of alpha-mannose linkages in the sample. The column behavior, alpha-mannosidase sensitivity, and likely subunit size limitation of a MOS sample (BioMOS®) is shown in FIG. 2.

Example 3

A female patient had been experiencing urinary tract infections since 1999. Episodes were very painful and invariably occurred about 48 hours after having sex. Antibiotics (Bactrin DS® or Cipro® 500 mg, or its generic equivalent, 1 tablet taken twice daily for five days) would quickly relieve symptoms. This pattern persisted for 6 years.

During an episode of UTI symptoms, a D-Mannose preparation, D-Mannose with CranActin™ (500 mg Mannose, 200 mg cranberry extract, Solaray), was administered—one or two per hour (with large quantities of water). This mitigated UTI symptoms, but did not completely resolve them. GI side effects (nausea, lower GI cramps) accompanied.

Example 4

During an episode of UTI symptoms (urge to urinate; severe burning with urination; blood in urine), 100 mg MOS was administered to a female patient (weighing approximately 50 kg) as a tablet (BioMOS® tablets, Alltech)-1 tablet before and after sex, plus three tablets per day. Symptoms were relieved.

Example 5

100 mg MOS was administered to a female patient (weighing approximately 50 kg) as a tablet (BioMOS® tablets, Alltech), 2 times per day for two months. The patient had reported typically experiencing severe UTI symptoms related to having sex. Administration of MOS prevented the appearance of symptoms, even with ample activity that would normally generate symptoms.

Example 6

Beginning during a symptom-free period, 100 mg MOS was administered to a female patient (weighing approximately 50 kg) as a tablet (BioMOS® tablets, Alltech), once per day plus one pill with sex. However, after three weeks, UTI symptoms reappeared. Two MOS tablets were taken two hours apart and symptoms were eliminated.

Example 7

During a symptom-free period, 500 mg of MOS was administered as a capsule (capsules prepared from bulk CitriStim™, Archer Daniels Midland Alliance Nutrition, Inc., Quincy, Ill.; 1 or 2 capsules daily). However, on the fifth day, UTI symptoms (urge to urinate; severe burning with urination; blood in urine) appeared. Two capsules (CitriStim) were administered (three hours apart), followed 2 hours later by 100 mg MOS in tablet form (BioMOS® tablets, Alltech). Symptoms became manageable, but returned the following day. Two MOS tablets were administered that morning (4 hours apart). In the late afternoon, a CitriStim capsule was administered, and one capsule was administered twice the following day. The UTI symptoms were eliminated.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a," "or," and "the" include plural referents unless the context clearly dictates otherwise. Thus, for example, reference to "an attenuated sporozoite vaccine" includes a plurality of such sporozoites and reference to "the agent" includes reference to one or more agents and equivalents thereof known to those skilled in the art, and so forth.

All numbers expressing quantities of ingredients, reaction conditions, % purity, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Obviously, many modifications and variations of the present invention are possible in light of the above teachings. It is therefore to be understood that, within the scope of the appended claims, the invention many be practiced otherwise than as specifically described.

All references provided herein are explicitly incorporated by reference into the present application.

In the foregoing, the present invention has been described with reference to suitable embodiments, but these embodiments are only for purposes of understanding the invention and various alterations or modifications are possible so long as the present invention does not deviate from the claims that follow.

What is claimed is:

1. A method for treating symptoms of urinary tract infections in a human patient in need of treatment for a urinary tract infection comprising oral administration of a dose of at least 10 milligrams, but no more than 20 milligrams of a mannan oligosaccharide (MOS) per kilogram of patient weight wherein covalent mannose-mannose bonds of said MOS are primarily in the alpha configuration.

2. The method of claim 1 wherein said dosage is 10 milligrams per kilogram of patient weight.

3. The method of claim 1 wherein said dosage is administered between one and three times daily.

4. The method of claim 3 further comprising daily administration for at least two days.

5. The method of claim 4 comprising administration for at least one week.

6. A method for relieving symptoms of urinary tract infections in a human patient in need of treatment for a urinary tract infection comprising oral administration of a dose of at least 10 milligrams, but no more than 20 milligrams of a yeast outer cell wall extract per kilogram of patient weight.

7. The method of claim 6 further comprising the degradation of said cell wall to mannan oligosaccharides.

8. The method of claim 7 wherein said oligosaccharides consist of no more than 10 subunits.

* * * * *